United States Patent
Eriksson et al.

(10) Patent No.: US 10,023,659 B2
(45) Date of Patent: *Jul. 17, 2018

(54) PROCESSES FOR THE PRODUCTION OF CHEMICALLY-MODIFIED HEPARINS

(71) Applicant: DILAFOR AB, Solna (SE)

(72) Inventors: Per-Olov Eriksson, Strängnäs (SE); Erik Yngve Holmer, Stockholm (SE)

(73) Assignee: Dilafor AB, Solna (SE)

( * ) Notice: Subject to any disclaimer, the term of this patent is extended or adjusted under 35 U.S.C. 154(b) by 83 days.

This patent is subject to a terminal disclaimer.

(21) Appl. No.: 14/898,862

(22) PCT Filed: Jun. 19, 2014

(86) PCT No.: PCT/GB2014/051878
§ 371 (c)(1),
(2) Date: Dec. 16, 2015

(87) PCT Pub. No.: WO2014/202982
PCT Pub. Date: Dec. 24, 2014

(65) Prior Publication Data
US 2016/0137754 A1  May 19, 2016

(30) Foreign Application Priority Data

Jun. 19, 2013 (GB) .................................. 1310928.5

(51) Int. Cl.
*A61K 31/727* (2006.01)
*C08B 37/00* (2006.01)

(52) U.S. Cl.
CPC ........ *C08B 37/0075* (2013.01); *A61K 31/727* (2013.01)

(58) Field of Classification Search
CPC .......................... A61K 31/727; C08B 37/0075
USPC .............................................. 514/56; 536/21
See application file for complete search history.

(56) References Cited

U.S. PATENT DOCUMENTS

| | | |
|---|---|---|
| 4,990,502 A | 2/1991 | Lormeau et al. |
| 5,767,269 A | 6/1998 | Hirsh et al. |
| 6,569,840 B1 | 5/2003 | Yamashina et al. |
| 2006/0040896 A1 | 2/2006 | Kennedy |
| 2007/0021378 A1 | 1/2007 | Varki et al. |
| 2010/0324276 A1 | 12/2010 | Sundaram et al. |

FOREIGN PATENT DOCUMENTS

| | | | |
|---|---|---|---|
| EP | 0735050 A2 * | 10/1996 | ............ C08B 37/10 |
| EP | 1059304 A1 | 12/2000 | |
| EP | 0735050 B1 | 9/2002 | |
| JP | 05/508184 A | 11/1993 | |
| JP | 2011/503001 A | 1/2011 | |
| WO | 92/18545 A1 | 10/1992 | |
| WO | 2009/007224 A1 | 1/2009 | |
| WO | 2009/059283 A1 | 5/2009 | |
| WO | 2013/095276 A1 | 6/2013 | |
| WO | 2013/095279 A1 | 6/2013 | |

OTHER PUBLICATIONS

Lau et al, Clinical and Experimental Pharmacology and Physiology, 2010, 37(4), 417-421.*
Ekman-Ordeberg et al., "Does Low Molecular Weight Heparin Shorten Term Labor?," Acta Obstetricia et Gynecologica 89:147-150 (2010).
European Pharmacopeia 7.0, European Directorate for the Quality of Medicines & Healthcare, monograph 0828:2151-2153.
Lau et al., "Inhibitors of Slit Protein Interactions with the Heparan Sulphate Proteoglycan Glypican-1: Potential Agents for the Treatment of Spinal Cord Injury," Clinical and Experimental Pharmacology and Physiology 37:417-421 (2010).
Mulloy et al., "Molecular Weight Measurements of Low Molecular Weight Heparins by Gel Permeation Chromatography," Thrombos Haemostas. 77:668-674 (1997).
International Search Report and Written Opinion for International Application No. PCT/GB2014/051787, (dated Oct. 1, 2014).

* cited by examiner

*Primary Examiner* — Ganapathy Krishnan
(74) *Attorney, Agent, or Firm* — LeClairRyan PLLC

(57) ABSTRACT

The present invention relates to a process for the production of heparin derivatives having an average molecular weight of from about 4.6 to about 6.9 kDa and an anti-factor Xa activity of less than about 10 IU/mg, comprising the steps of oxidation of unfractionated heparin, depolymerisation and reduction of resulting terminal groups.

17 Claims, 1 Drawing Sheet

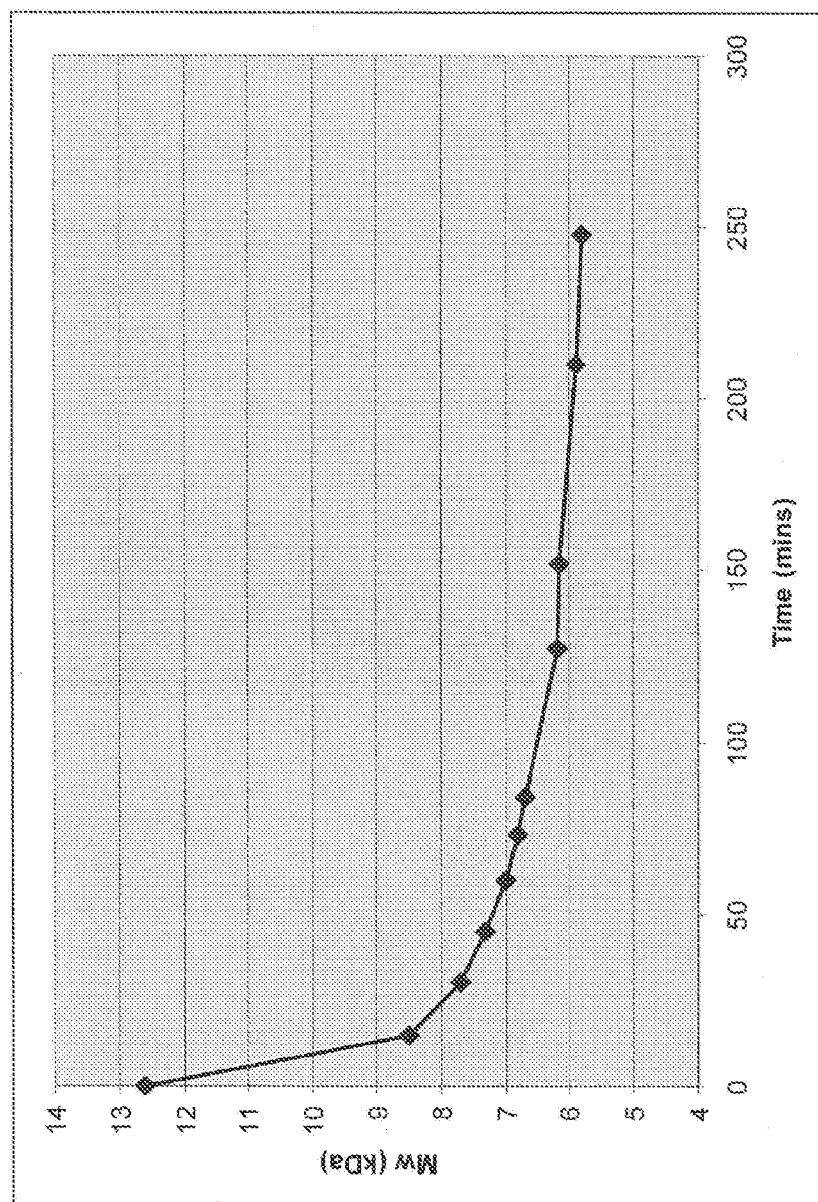

PROCESSES FOR THE PRODUCTION OF CHEMICALLY-MODIFIED HEPARINS

This application is a national stage application under 35 U.S.C. § 371 of PCT Application No. PCT/GB2014/051878, filed Jun. 19, 2014, which claims the priority benefit of GB Patent Application No. 1310928.5, filed Jun. 19, 2013.

FIELD OF THE INVENTION

The present invention relates to new processes. In particular, it relates to new processes for the preparation of chemically-modified glycosaminoglycans, such as chemically-modified heparin.

BACKGROUND

The listing or discussion of an apparently prior-published document in this specification should not necessarily be taken as an acknowledgement that the document is part of the state of the art or common general knowledge.

Heparin is a polydisperse, naturally occurring polysaccharide that inhibits coagulation, the process whereby thrombosis occurs. Heparin consists of unbranched polysaccharide chains of varying lengths and molecular weights. Chains of molecular weight from 5000 to over 40,000 daltons make up pharmaceutical grade heparin.

Heparin, which is typically derived from natural sources such as porcine intestine or bovine lung tissue, can be administered therapeutically for prevention and treatment of thrombosis. However, the effects of unfractionated heparin can be difficult to predict. Therefore, during treatment of thrombosis with unfractionated heparin, coagulation parameters must be monitored very closely to prevent over- or under-anticoagulation.

Numerous brands of heparins and low molecular weight heparins (LMWH), such as dalteparin and enoxaparin, are available for the treatments that rely on their anti-coagulant activity. A large number of in vitro and animal experimental investigations, and even clinical trials, indicate that heparin and its derivatives have beneficial properties others than those related to its anticoagulant effect. However, existing heparins and LMWH are not suitable for treating other medical conditions because of the bleeding risk associated with the anticoagulant effect.

The LMWH dalteparin has been shown to decrease protracted labour in women receiving prophylaxis for deep venous thrombosis. The mechanism is believed to involve dalteparin-induced increased levels of interleukins resulting in a favourable inflammatory reaction that promotes ripening of the cervix. Further, dalteparin has been shown to increase contractility of the uterus (*Acta Obstetricia et Gynecologica*, 2010; 89:147-150). However, heparin and LMWH are not suitable for preventing or treating such maladies for a number of reasons.

Firstly, heparin and LMWH have significant, well known anti-coagulant effects that restrict their use in late pregnancy and during delivery, both for prophylactic and acute use, due to the bleeding risk. For example, the use of dalteparin is strictly contraindicated when epidural anaesthesia is given, a measure frequently taken during child birth.

Secondly, heparin, and to some extent LMWH, has been associated with heparin-induced thrombocytopenia, a severe immune-mediated drug reaction that can occur in any patient exposed to heparin. It is a potentially devastating pro-thrombotic disease caused by heparin-dependent antibodies that develop either after a patient has been on heparin for five days or more, or if the patient has had previous heparin exposure.

Another undesirable possible effect of long term treatment with heparin is that it may induce demineralization of bones and cause osteoporosis.

There have been many attempts to eradicate or reduce the anticoagulant activity of heparins or low molecular weight heparins in order to provide low anticoagulant heparins (LAHs) which aim to benefit from other potential clinical effects from the heparin chains than the anticoagulant effect, without carrying the risk of undesirable effects associated with heparin, predominantly bleeding. However, there is limited clinical experience of this type of heparins and so far no such products have been allowed for clinical use.

Heparin exerts its anticoagulant activity primarily through high-affinity binding to, and activation of, the serine proteinase inhibitor, antithrombin (AT). AT, an important physiological inhibitor of blood coagulation, neutralizes activated coagulation factors by forming a stable complex with these factors. Binding of a specific pentasaccharide within the polysaccharide chains of heparin causes a conformational change in AT that dramatically enhances the rate of inhibition of coagulation factors, thereby attenuating blood coagulation and the formation of blood clots.

European patent application EP 1 059 304 discloses enzymatically degraded or oxidized heparin resulting in a product with low anticoagulant effect, having an average molecular weight of 9 to 13 kDa, which is suggested for the treatment of neurodegenerative diseases.

U.S. Pat. No. 4,990,502 demonstrates one way of treating native heparin to cleave the pentasaccharide residues responsible for the anticoagulant effect and a following depolymerisation that results in a low anticoagulant, low molecular weight heparin with a an average molecular weight 5.8 to 7.0 kDa. However, in U.S. Pat. No. 4,990,502 time consuming methods, such as dialysis for about 15 hours, are used to terminate the oxidation process. Such processes can affect the molecular weight distribution of the final product and give rise to unfavourable structural variants, which can be seen by $^1$H NMR.

Controlling the molecular weight and the length of the polysaccharide chains is crucial to obtain the desired biological effect of the compound. The bioavailability of long chain heparins after subcutaneous dosing is low and the possibility of heparin induced thrombocytopenia (HIT) induction is also positively correlated to the chain lengths. To reduce these clinically undesired properties the heparin derivative should not be of full length. Heparin chains of certain molecular weight can be obtained by fractionation of standard heparin. However, the production of heparin derivatives of intermediate or low molecular weight by fractionation methods such as gel-filtration, alcohol precipitation and ion exchange chromatography is associated with a significant waste of raw material, as high molecular mass heparins are discarded.

As disclosed herein, heparin derivatives having low anticoagulant activity can be prepared using a process comprising the steps of oxidation of unfractionated heparin, depolymerisation and reduction of resulting terminal groups, which derivatives are of use in decreasing the duration of protracted labour.

In particular, we have unexpectedly found that levels of unwanted structural modifications occurring during the preparation of heparin derivatives using such processes can be minimised by controlling the time elapsed between the oxidation and reduction steps. Further, we have found that the average molecular weight of the resulting heparin derivative can be controlled by monitoring the progress of the depolymerisation step (or by reference to a previously-performed process) and adjusting the duration of the depolymerisation step accordingly.

International (PCT) application number PCT/SE2012/051433 (published as WO 2013/095279) discloses a process for the preparation of derivatives of unfractionated heparin comprising oxidation, depolymerisation and reduction of terminal groups, which derivatives have low anti-coagulant activity and are of use in decreasing the duration of protracted labour. However, this international application does not refer to monitoring the progress of the depolymerisation step to control the average molecular weight of the resulting heparin derivative.

DISCLOSURE OF THE INVENTION

In a first aspect of the invention, there is provided a process for the preparation of a heparin derivative having an average molecular weight of from about 4.6 to about 6.9 kDa and an anti-factor Xa activity of less than about 10 IU/mg, comprising the consecutive steps of:
(i) oxidising an acidic aqueous solution of unfractionated heparin by addition of an oxidising agent;
(ii) depolymerising the oxidised heparin by subjecting the product of step (i) to alkali to form an alkaline solution;
(iii) maintaining said solution from step (ii) at an alkaline pH for a period of time required to provide depolymerised heparin with a molecular weight within the aforesaid range; and
(iv) reducing terminal aldehyde groups of said depolymerised heparin by addition of a hydride reducing agent to the solution obtained from step (iii),
wherein the period of time between the completion of step (i) and the start of step (iv) is controlled in order to minimise the effect of residual oxidising agents; and
wherein said period of time in step (iii) is determined by analysis of said solution, or by reference to a previously-performed substantially identical step (iii).

The skilled person will understand that any embodiment of the invention as described herein may be combined with any one or more other embodiment in order to provide a further embodiment of the invention. All such combinations of embodiments described herein are specifically contemplated. Thus, references to any aspect of the invention will include references to any embodiment, or combination of embodiments, thereof.

As used herein, the term "about" may refer to a value that is with 10% (particularly, within 5%, such as within 1%) of the value specified. At each occurrence, embodiments of the invention include those wherein the term "about" is removed.

The skilled person will understand that the reference to steps being "consecutive" indicates that they are performed sequentially in the order shown. In a particular embodiment, the steps may be performed in a direct sequence, for example without intervening steps. Therefore, in a particular embodiment, the process defined in the first aspect of the invention may be referred to as "consisting" of the consecutive steps as referred to in the first aspect of the invention (or any embodiment, or combination of embodiments, thereof).

In a particular embodiment, the process defined in the first aspect of the invention may be performed in a single reaction vessel (a so-called "one-pot" process).

The Heparin Derivative

The process defined in the first aspect of the invention allows for the production of a heparin derivative having an average molecular weight (Mw) of from about 4.6 to about 6.9 kDa and an anti-factor Xa activity of less than about 10 IU/mg, using the current International standards for Low Molecular Weight Heparins.

For the avoidance of doubt, the skilled person will understand that the term "average molecular weight" as referred to herein refers to a weight average molecular weight.

The average molecular weight of the heparin derivative may be determined using techniques known to those skilled in the art. For example, the average molecular weight may be determined by analysis of a sample of the heparin derivative obtained from the process defined in the first aspect of the invention using high performance liquid chromatography (HPLC), such as gel permeation chromatography HPLC (GPC-HPLC).

In particular, molecular weight analysis may be performed in accordance with the Ph Eur Procedure for gel permeation chromatography of Low-Molecular-Mass Heparin (monograph 0828), as modified by Mulloy et al. ("*Molecular Weight Measurements of Low Molecular Weight Heparins by Gel Permeation Chromatography*", Thrombos. Haemostas. 77, 1997, 668-674), wherein the chromatographic system is calibrated utilizing the International Molecular Weight Standard for Low-Molecular-Weight Heparin.

In a particular embodiment, the heparin derivative prepared by the process defined in the first aspect of the invention has an average molecular weight of from about 5.0 to about 6.0 kDa (such as about 5.2 to about 5.9 kDa, for example about 5.3 to about 5.8 kDa or, alternatively, about 5.7 to about 6.3 KDa).

Particular heparin derivatives prepared by the process defined in the first aspect of the invention include those having an average molecular weight of about 5.8 kDa, about 5.6 kDa or about 5.3 kDa.

In a particular embodiment, the heparin derivative prepared by the process defined in the first aspect of the invention comprises polysaccharides with a distribution of cumulative molecular weights as indicated in Table 1 below.

TABLE 1

| Molecular mass, kDa | Cumulative weight, % |
|---|---|
| >10 | 4-15 |
| >8 | 10-25 |
| >6 | 22-45 |
| >3 | >70 |

In a particular embodiment, the heparin derivative produced by the process defined in the first aspect of the invention may consist of molecules at least 70% of which have a molecular weight of greater than about 3 kDa.

The process defined in the first aspect of the invention allows for the production of heparin derivatives having low anti-coagulation properties.

The skilled person will understand that the anti-coagulant activity of heparin and the like results from high-affinity binding to, and activation of, the serine proteinase inhibitor, antithrombin (AT). Activated AT in turn acts to form stable complexes with various coagulation factors and thus neutralise their effect. It is therefore possible to quantify anti-coagulant properties by determining the activity of these coagulation factors.

The skilled person will understand that the anticoagulation activity of the heparin derivative produced by the process defined in the first aspect of the invention may be measured by determining the activity of the coagulation factors Xa and IIa.

In a particular embodiment, the heparin derivative produced by the process defined in the first aspect of the invention have an anti-factor Xa and an anti-factor IIa activity of less than 10 IU/mg.

In a more particular embodiment, the heparin derivative produced by the process defined in the first aspect of the invention may have an anti-factor Xa activity of less than 5 IU/mg and/or an anti-factor IIa activity of less than 5 IU/mg. For example, the heparin derivative produced by the process defined in the first aspect of the invention may have an anti-factor Xa activity of less than 5 IU/mg and an anti-factor IIa activity of less than 5 IU/mg.

In a more particular embodiment, the heparin derivative produced by the process defined in the first aspect of the invention may have an anti-factor Xa activity of less than 1 IU/mg and/or an anti-factor IIa activity of less than 1 IU/mg.

Determination of anticoagulant activity, anti-factor IIa and anti-factor Xa may be performed according to the Ph Eur procedure for Low-Molecular-Mass Heparin (monograph 0828), wherein the International Activity Standard for Low-Molecular-Weight Heparin is used to calibrate the system.

In a particular embodiment, the heparin derivatives produced using the process defined in the first aspect of the invention may have no detectable anticoagulation activity, as measured by analytical methods known in the art.

The skilled person will appreciate that the process defined in the first aspect of the invention allows for the residues present in unfractionated heparin to be oxidised, depolymerised and reduced, which in turn provides a heparin derivative consisting of modified residues and having a low molecular weight.

In a particular embodiment, the polysaccharide chains present in the heparin derivative are essentially free of chemically intact saccharide sequences mediating the anticoagulant effect (e.g. ≤1% of the polysaccharide chains present in the heparin derivative comprise said chemically intact saccharide sequences, as detectable by NMR).

In a further embodiment, the predominantly occurring disaccharide in the heparin derivative is as shown in formula I below.

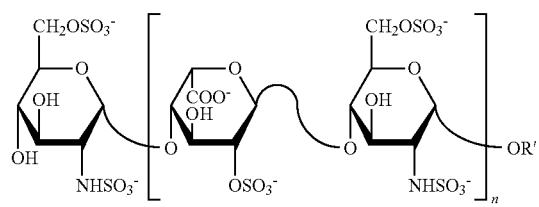

wherein

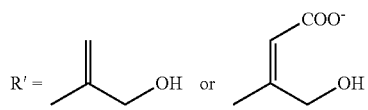

and n is an integer from 2 to 20.

As used herein, the term "predominantly occurring" may be understood to refer to the respective feature occurring in the majority (i.e. greater than 50%, for example greater than 60% or, particularly, greater than 80%) of instances.

In a further embodiment, the polysaccharide chains have from 2 to 20 (n in formula I) disaccharide units corresponding to molecular weights between 1.2 and 12 kDa.

The skilled person will also understand that the process defined in the first aspect of the invention allows for the production of a heparin derivative wherein the sulphate groups present in the unfractionated heparin are retained.

In a particular embodiment, there is provided a process for preparing a heparin derivative wherein at least about 70% (such as at least about 80%, e.g. at least about 90%) of the sulphate groups are present.

As described herein, the process defined in the first aspect of the invention allows for the production of a heparin derivative having a low level of unwanted structural modifications, which unwanted structural modifications result from the action of residual oxidising agents.

As used herein, the term "residual oxidising agents" may refer to one or more species present in the process after the completion of step (i) that are capable of further oxidising the heparin derivative obtained from that step.

The presence of these species has been found to lead to unwanted structural modifications in the heparin derivative. In particular, these unwanted structural modifications have been found to result from non-specific depolymerisation of the heparin derivative, i.e. depolymerisation other than that mediated by alkaline beta elimination (i.e. in step (ii) as defined herein).

Such non-specific depolymerisation processes may lead to the formation of a heparin derivative having a lack of predictability in respect of its molecular weight and poor stability, and may lead to discolouration (which may increase upon storage).

In particular, unwanted structural modifications as referred to herein may be characterised by the presence of unidentified chemically-modified heparin residues. For example, these unidentified chemically-modified heparin residues may be characterised by signals in the 5.0 ppm to 6.5 ppm region of the $^1$H NMR spectrum of the heparin derivative. More particularly, such unidentified chemically-modified heparin residues may be characterised by the presence of a double bond at the C4-C5 position of a monosaccharide unit of the polysaccharide, which may be identified by signals in the $^1$H NMR spectrum of the heparin derivative at between about 5.0 and about 6.5 ppm (e.g. at about 5.95 ppm and about 6.15 ppm).

In a particular embodiment, there is provided a process for preparing a heparin derivative having signals in the 5.0 ppm to 6.5 ppm region of the corresponding $^1$H NMR spectrum with an intensity (% ratio) of ≤5 about 4% (e.g. about 3%, such as ≤about 2.5%) relative to the signal at 5.42 ppm of the $^1$H NMR spectrum of unfractionated heparin.

In a more particular embodiment, there is provided a process for preparing a heparin derivative having signals at 5.95 ppm and 6.15 ppm in the corresponding $^1$H NMR spectrum with an intensity (% ratio) of ≤about 4% (e.g. ≤about 3%, such as ≤about 1%) relative to the signal at 5.42 ppm of the $^1$H NMR spectrum of unfractionated heparin.

In a further embodiment, there is provided a heparin derivative (e.g. as defined in respect of the first aspect of the invention) obtainable using a process as defined in the first aspect of the invention.

Oxidation

The process defined in the first aspect of the invention comprises the step of:

(i) oxidising an acidic aqueous solution of unfractionated heparin by addition of an oxidising agent.

As used herein, the term "aqueous solution" refers to a solution in water. In particular, the reference to an aqueous solution of unfractionated heparin may refer to a solution in water wherein at least 90% (particularly, at least 95%, such as at least 99%) of the heparin is dissolved. More particularly, it may refer to a solution containing no undissolved heparin as observed by visual inspection.

As used herein in respect of step (i) of the process of the first aspect of the invention, the reference to an acidic solution will be understood to mean a solution having a pH of less than 7 (e.g. less than about 6). In particular, it may refer to a solution having a pH of from about 3 to about 6 (e.g. from about 3.5 to about 6, such as about 4.5 to about 5.5).

The skilled person will understand that the pH of the aqueous solution may be adjusted either before or after (e.g. before) the addition of oxidising agent.

In a particular embodiment, the pH of the solution is maintained until the completion of the oxidation (i.e. the completion of step (i) as defined herein).

The skilled person will understand that the pH of the aqueous solution may be adjusted and/or maintained by the addition of a suitable acid, such as a suitable strong acid (e.g. a mineral or organic acid, such as a mineral acid, having a pKa value of less than about 5, such as from about 1 to about 5).

In a particular embodiment, the pH of the solution may be adjusted to and maintained at about 4.5 to about 5.5, such as at about 5.

In a particular embodiment, the concentration of heparin in solution is from about 10 to about 20% (e.g. about 15%) weight of heparin by volume of water.

The skilled person will understand that the reference to an oxidising agent is intended to refer to an agent that is capable of oxidising unfractionated heparin. In particular, the skilled person will understand that the reference to an oxidising agent may refer to an agent capable of oxidative cleavage of vicinal diols in unfractionated heparin, i.e. to result in corresponding aldehyde moieties.

For the avoidance of doubt, the reference to oxidising an acidic aqueous solution of unfractionated heparin by addition of an oxidising agent (i.e. as referred to in step (i) as defined herein) may refer to oxidising an acidic aqueous solution of unfractionated heparin by addition of an oxidising agent capable of cleaving vicinal diol moieties therein.

In a particular embodiment, the oxidising agent may be a suitable periodate (such as sodium metaperiodate) or permanganate (such as potassium permanganate). In a more particular embodiment, the oxidising agent is sodium metaperiodate.

The skilled person will appreciate that the oxidising agent, such as sodium metaperiodate, may be added to the aqueous solution either in one portion, step-wise or continuously. Moreover, the oxidising agent may be added as a solid or as a solution (e.g. an aqueous solution).

In a particular embodiment, the amount of oxidising agent, such as sodium metaperiodate, added will be from about 15 to about 35% by weight of the amount of heparin present in the solution (e.g. about 25% by weight of the amount of heparin present in the solution).

In a particular embodiment, step (i) of the process of the first aspect of the invention may be performed at a reduced temperature.

As used herein, the skilled person will understand that the term "reduced temperature" refers to a temperature that is below ambient (room) temperature, i.e. below about 25° C. (e.g. below about 20° C.). The initial temperature of the solution may be adjusted prior to, or immediately following, the addition of the oxidising agent.

In a particular embodiment, the temperature of step (i) of the process of the first aspect of the invention may be lowered to about 5° C. for the last two hours of reaction.

In a more particular embodiment, step (i) of the process of the first aspect of the invention may be performed at a temperature below room temperature but greater than about 10° C., for example at a temperature of about 13° C. to about 17° C.

In a more particular embodiment, step (i) of the process of the first aspect of the invention may be performed at a temperature of about 13° C. to about 17° C. and then cooled to a temperature of about 5° C. for the final about two hours of the reaction.

In a particular embodiment, step (i) of the process of the first aspect of the invention may be protected from light.

In a particular embodiment, step (i) of the process of the first aspect of the invention is performed for a duration (i.e. a period of time) sufficient to allow for complete oxidation of the heparin, which period may be from about 18 to about 26 hours (for example, from about 18 to about 24 hours).

As used herein, the reference to achieving complete oxidation may refer to obtaining an oxidised derivative wherein at least about 90% (e.g. at least about 95%, such as at least about 99%) of non-sulphated vicinal diol moieties (e.g. in the iduronic and glucuronic acid residues of heparin) have been converted to corresponding aldehydes, for example as determined by GPC-HPLC and NMR.

The skilled person will understand that the progress of step (i) of the process of the first aspect of the invention can be controlled by adjusting the temperature and the duration of the reaction.

The skilled person will understand that the progress of step (i) of the process of the first aspect of the invention can be followed by analysis of samples taken from the solution, for example using GPC-HPLC, and the period of time required in respect of step (i) adjusted accordingly. In particular, step (i) of the process of the first aspect of the invention can be followed and the duration adjusted in order to minimise depolymerisation (as identified by a decrease in average molecular weight).

Thus, in a particular embodiment, step (i) of the process defined in the first aspect of the invention requires oxidising said heparin by addition of sodium metaperiodate to the solution obtained in step (i), and then maintaining the resulting solution at a pH of from about 4.5 to about 5.5 and optionally at a reduced temperature, for a period of from about 18 to about 26 hours.

Thus, in a particular embodiment, the process defined in the first aspect of the invention comprises the step of:

(i) oxidising an aqueous solution of unfractionated heparin by addition of sodium metaperiodate, at a pH of from about 4.5 to about 5.5 and at reduced temperature.

Depolymerisation

The process defined in the first aspect of the invention comprises the steps of:

(ii) depolymerising the oxidised heparin by subjecting the product of step (i) to alkali to form an alkaline solution; and (iii) maintaining said solution from step (ii) at an alkaline pH for a period of time required to provide depolymerised heparin with a molecular weight within the aforesaid range (i.e. as defined in the first aspect of the invention), wherein said period of time in step (iii) is determined by analysis of said solution, or by reference to a previously-performed substantially identical step (iii).

The skilled person will understand that in steps (ii) and (iii) of the process, as defined in the first aspect of the invention, depolymerisation of the oxidised heparin obtained from step (i) is achieved by alkaline beta elimination.

As used herein in respect of steps (ii) and (iii) of the process defined in the first aspect of the invention, the reference to forming an alkaline solution will be understood to refer to adjusting the pH of the solution to from about 8 to about 13. In particular, it is important that the pH of the solution is kept lower than about 13.

The pH of the solution may be adjusted and/or maintained by addition of a suitable base, for example an alkaline metal hydroxide (e.g. sodium hydroxide) or alkaline metal carbonate (e.g. sodium carbonate).

In particular embodiment, the pH of the solution is adjusted to from about 10.5 to about 11.5, for example, by the addition of an alkaline metal hydroxide (such as, sodium hydroxide), which may be in the form of an aqueous solution (for example, a 1 to 4 molar solution).

The skilled person will understand that pH of the solution may be adjusted at reduced temperature. In a particular embodiment, in step (ii) of the process of the first aspect of the invention, the pH of the solution is adjusted whilst the solution is at a temperature of about 5° C. to about 10° C.

The skilled person will understand that the progress of the depolymerisation reaction may be controlled by adjusting the temperature in step (iii) of the process of the first aspect of the invention. For example, the solution may be maintained at a temperature of from about 5° C. to about 25° C. (e.g. at about 5° C. to about 10° C.).

The skilled person will appreciate that the average molecular weight obtained in the depolymerisation step will determine the average molecular weight of the heparin derivative produced by the process defined in the first aspect of the invention. Thus, the solution is maintained at the required pH (and, optionally, at the required temperature) for a period of time required to provide depolymerised heparin having the required molecular weight within the aforesaid range (i.e. about 4.6 to about 6.9 kDa).

The skilled person will understand that the period of time required to obtain a depolymerised heparin derivative having the required average molecular weight will depend on the conditions used in steps (ii) and (iii) of the process of the first aspect of the invention. Under conditions as described herein above, the period of time will typically be a maximum of about four hours.

As referred to herein, the period of time required to obtain a depolymerised heparin derivative having the required average molecular weight may be determined by analysis of the solution using techniques known to those skilled in the art. In particular, the average molecular weight of the depolymerised heparin derivative may be monitored by the taking of samples from the reaction mixture and analysis of those samples using various chromatography-based techniques (such as GPC-HPLC).

Thus, the reference to the period of time required to obtain a depolymerised heparin derivative having the required average molecular weight may refer to the period of time required in order for analysis of the solution to confirm that the depolymerised heparin derivative is of the required molecular weight.

In a particular embodiment, the analysis of the solution is performed using repeated GPC-HPLC analysis (e.g. at intervals of about 30 minutes). Such analysis may be performed using techniques as described herein, e.g. in accordance with the Ph Eur Procedure for gel permeation chromatography of Low-Molecular-Mass Heparin (monograph 0828), as modified by Mulloy et al. ("*Molecular Weight Measurements of Low Molecular Weight Heparins by Gel Permeation Chromatography*", *Thrombos. Haemostas.*, 77, 1997, 668-674), wherein the chromatographic system is calibrated utilizing the International Molecular Weight Standard for Low-Molecular-Weight Heparin.

Alternatively, the period of time required to obtain a depolymerised heparin derivative having the required average molecular weight may be determined by reference to a previously-performed substantially identical step (iii).

As used herein, the reference to a substantially identical step (iii) will be understood to refer to a previously-performed process step (i.e. reaction) corresponding to step (iii) of the process of the invention, which process step was performed using substantially identical reagents and under substantially identical conditions to step (iii) of the process of the first aspect of the invention.

As used herein, the reference to substantially identical conditions will be understood to refer to conditions (such as pH, concentration of reagents and temperature) that are within a 10% variation of (e.g. within a 5% variation of, such as within a 1% variation of) those used in the present step (iii) of the process of the first aspect of the invention.

As used herein, the reference to substantial identical reagents will include a reference to the use of a substantially identical heparin derivative as obtained from steps (i) and (ii) of the process of the first aspect of the invention.

The skilled person will appreciate that the reference to previously-performed step (iii) using a substantially identical heparin derivative may refer to a step (iii) that was performed following substantially identical steps (i) and (ii).

As used herein, the reference to a substantially identical steps (i) and (ii) will be understood in the same manner as the reference to the substantially identical step (iii).

In particular, the reference to a substantially identical step (i) will refer to a previously-performed step (i) starting with substantially identical unfractionated heparin.

As used herein, the reference to substantially identical unfractionated heparin may refer to unfractionated heparin obtained from the same supplier as the heparin used in the present process of the first aspect of the invention. In particular, the reference to substantially identical unfractionated heparin may refer to unfractionated heparin taken from the same batch as the heparin used in the present process of the first aspect of the invention.

As used herein in respect of substantially identical steps (i), (ii) and (iii), the reference to substantially identical reagents will also include a reference to the use of oxidising and/or reducing agents that are chemically the same as, or functionally equivalent to, the reagents used in the present process of the first aspect of the invention.

The skilled person will understand that the period of time required to obtain a depolymerised heparin derivative having the required average molecular weight may be taken to be about the same as, or about the same as an extrapolation of, the time required to obtain a particular average molecular weight in the substantially identical step (iii) as referred to herein.

Once the period of time required in order to obtain a depolymerised heparin derivative having the required average molecular weight has elapsed, the depolymerisation reaction may be terminated. In a particular embodiment, the depolymerisation reaction may be terminated by forming an acidic solution.

Thus, in a particular embodiment, the process of the first aspect of the invention further comprises (i.e. between steps (iii) and (iv)) the step of:
(iiia) subjecting the solution obtained from step (iii) to acid to form an acidic solution.

As used herein in respect of step (iii) of the process of the first aspect of the inventions (and in respect of the embodiment thereof referring to step (iiia)), the reference to forming an acidic solution refers to adjusting the pH of the lower than 7 (such as from about 4 to about 6.5, e.g. about 5.5 to about 6.5), by the addition of a suitable acid as herein before defined (e.g. HCl, such as a 4 molar solution of HCl).

Thus, in a particular embodiment, the process defined in the first aspect of the invention comprises the steps of:
(ii) depolymerising the oxidised heparin by subjecting the product of step (i) to alkali to form a solution having a pH of from about 8 to about 13 (e.g. from about 10.5 to about 11.5); and
(iii) maintaining said solution from step (ii) at an alkaline pH for a period of time required to provide depolymerised heparin with a molecular weight within the aforesaid range (i.e. as defined in the first aspect of the invention); and
(iiia) subjecting the solution obtained from step (iii) to acid to form a solution having a pH of from about 5.5 to about 6.5,
wherein said period of time in step (iii) is determined by analysis of said solution, or by reference to a substantially identical step (iii).

Reduction

The process defined in the first aspect of the invention comprises the step of:
(iv) reducing terminal aldehyde groups of said depolymerised heparin by addition of a hydride reducing agent to the solution obtained from step (iii).

The skilled person will understand that, in embodiments of the process of the first aspect of the invention that include step (iiia), step (iv) may refer to reducing terminal aldehyde groups of said depolymerised heparin by addition of a hydride reducing agent to the solution obtained from step (iiia).

The skilled person will appreciate that terminal aldehyde groups are formed as a product of the preceding depolymerisation step, i.e. steps (ii) to (iii) (or steps (ii) to (iiia), as appropriate).

The addition of the hydride reducing agent allows for the reduction of terminal aldehyde groups to form corresponding primary alcohols. The addition of the reducing agent also allows reduction (and therefore neutralisation) of residual oxidising agent as used in step (i), e.g. residual sodium metaperiodate or derivatives thereof. This residual oxidising agent may be present in solution in the form of periodate (and/or iodate) species, which may be reduced to less reactive iodine and iodide species.

The addition of a hydride reducing agent may also have the effect of increasing the pH of the solution (e.g. to from about 9 (e.g. about 10) to about 11).

In embodiments where the preceding depolymerisation step is terminated by the addition of acid, the addition of the hydride reducing agent will also react with and neutralise said acid. In such embodiments, the skilled person will understand that additional hydride reducing agent may be required to allow for such a reaction.

In a particular embodiment, the hydride reducing agent is a borohydride. In a more particular embodiment, the hydride reducing agent is sodium borohydride.

In a particular embodiment, the amount of hydride reducing agent, such as sodium borohydride, added is sufficient to allow for the complete reduction of terminal aldehyde groups and residual oxidising species.

The skilled person will appreciate that the amount of hydride required for the complete reduction of terminal aldehyde groups and residual oxidising species may be calculated based on the amount of heparin employed in the process and the degree of depolymerisation thereof, and the amount of oxidising agent employed.

The skilled person will understand that the hydride, such as sodium borohydride, may be added to the solution at reduced temperature (e.g. in order to counteract the exothermic nature of the reaction). In a particular embodiment, the hydride is added to the solution at a temperature of from about 5° C. to about 17° C.

The skilled person will appreciate that the hydride, such as sodium borohydride, may be added to the aqueous solution either in one portion, continuously or step-wise (i.e. by the addition of several smaller portions). Moreover, hydride may be added as a solid or as a solution (e.g. an alkali stabilised aqueous solution, such as an alkali stabilised aqueous solution of sodium borohydride).

Following the addition of the hydride, the reaction is maintained for a period sufficient for the complete reduction of terminal aldehyde groups to primary alcohols, optionally at a reduced temperature (e.g. at from about 5° C. to about 17° C.). For example, the solution may be maintained for a period of from about 4 to about 24 hours (e.g. from about 14 to about 20 hours).

As used herein, the reference to complete reduction of terminal aldehyde groups may refer to obtaining a heparin derivative is essentially free of aldehyde moieties, for example where 51% of aldehyde groups remain unreduced as determined by (e.g. $^{13}C$) NMR analysis.

Once the period of time required for reduction of terminal aldehyde groups has elapsed, the reduction reaction may be quenched. As used herein in respect of the reduction reaction (i.e. step (iv) as defined herein), the reference to the reaction being quenched will be understood by the skilled person to refer to termination of the reduction reaction through neutralisation of residual reducing agent.

The reduction reaction may be quenched using techniques known to those skilled in the art, such as by the addition of water or, particularly, aqueous acid (for example, an aqueous solution of a strong acid as defined herein, such as a 1 to 4 molar solution of HCl).

In a particular embodiment, the reduction reaction (i.e. step (iv) as defined herein) may be quenched by lowering the pH to form an acidic solution (e.g. by the addition of an aqueous solution of a strong acid as defined herein, such as a 1 to 4 molar solution of HCl).

Thus, in a particular embodiment, the process of the first aspect of the invention further comprises (i.e. following step (iv)) the step of:
(iva) quenching the reduction reaction by lowering the pH to form an acidic solution.

As used herein in respect of quenching the reduction reaction (e.g. in respect of step (iva), where applicable), the reference to lowering the pH to acidic solution refers to lowering the pH to below 7.

In a particular embodiment, the reaction is quenched by lowering the pH to about 2 to about 6 (such as from about 3 to about 5). In a more particular embodiment, the reaction is quenched by lowering the pH to about 4.

In a particular embodiment, the reaction is quenched by lowering the pH to acidic solution (e.g. to a pH of about 4) and maintaining the pH of the solution for more than about 30 minutes (e.g. about 45 to about 60 minutes).

Thus, in a particular embodiment, the process defined in the first aspect of the invention comprises the steps of:
(iv) reducing terminal aldehyde groups of said depolymerised heparin by addition of sodium borohydride to the solution obtained from step (iii); and
(iva) quenching the reduction reaction by lowering the pH to form an acidic solution.

Recovery of the Product

The skilled person will understand that the process of the invention may further comprise one or more step for the recovery and, if required, purification of the heparin derivative.

For example, the skilled person will understand that, where the process of the invention comprises the step of:
(iva) quenching the reduction reaction by lowering the pH to acidic solution,
the recovery of the heparin derivative may require the solution to be adjusted to neutral pH (i.e. about 7).

Thus, in a particular embodiment, where the process defined in the first aspect of the invention comprises step (iva) as defined herein, said process optionally further comprises (i.e. following step (iva)) the step of:
(ivb) adjusting the pH of the solution obtained from step (iva) to about neutral.

The pH of the solution may be adjusted by the addition of a suitable base, such as an alkaline metal (for example, an aqueous solution of sodium hydroxide) or, particularly, an alkaline metal carbonate (for example, an aqueous solution of sodium carbonate).

In a particular embodiment, the process of the first aspect of the invention further comprises (i.e. following step (iv) or, where applicable, step (iva) or (ivb)) the step of:
(v) recovering the heparin derivative from the solution obtained from step (iv) (or, where applicable, step (iva) or (ivb)).

As used herein, the reference to the recovery of the heparin derivative will be understood by the skilled person to refer to isolating at least a portion of the heparin derivative produced by the process of the first aspect of the invention from the solution obtained therein.

The recovery of the heparin derivative may be achieved using techniques known to those skilled in the art. Such techniques may include, in particular, precipitation of the heparin derivative from solution, which may be achieved by adjusting the polarity of the solution (e.g. by the addition of a polar solvent, such as ethanol).

The step of recovering the heparin derivative from solution may comprise (or be combined with) processes for further purification of the product, for example, through the removal of impurities and/or unwanted structural modifications.

Thus, in a particular embodiment, step (v) of the process defined in the first aspect of the invention, if carried out, may comprise one or more processes for the purification of the product.

The skilled person will understand that further purification of the heparin derivative may be achieved using techniques known to those skilled in the art. For example, such process may involve chromatography techniques, filtration, sequestration of impurities, centrifugation and/or drying processes.

Minimising Unwanted Structural Modifications

The process defined in the first aspect of the invention requires controlling the period of time between the completion of step (i) and the start of step (iv) in order to minimise the effect of residual oxidising agents.

As discussed herein, residual oxidising species may be present in the solution obtained in step (i) of the process defined in the first aspect of the invention, which species are then quenched by addition of the reducing agent in step (iv). In particular, the presence of these oxidising species has been found to lead to non-specific depolymerisation of the heparin derivative, i.e. depolymerisation other than that achieved by alkaline beta elimination (i.e. in step (iii)), which depolymerisation results in unwanted structural modifications in the heparin derivative.

Thus, the process defined in the first aspect of the invention may require controlling the period of time between the completion of step (i) and the start of step (iv) in order to minimise the effect of residual oxidising agents and minimise the level of resulting unwanted structural modifications in the heparin derivative.

In particular, the reference to controlling the period of time between the completion of step (i) and the start of step (iv) may refer to controlling said period of time in order to minimise the presence unwanted structural modifications in the heparin derivative as characterised by signals in the 5.0 ppm to 6.5 ppm region (in particular, at 5.95 ppm and 6.15 ppm) in the $^1$H NMR spectrum of the heparin derivative.

In a particular embodiment, there is provided a process for preparing a heparin derivative having signals in the 5.0 ppm to 6.5 ppm region of the corresponding $^1$H NMR spectrum with an intensity (% ratio) of ≤about 4% (e.g. ≤about 3%) relative to the signal at 5.42 ppm of the $^1$H NMR spectrum of unfractionated heparin.

In a more particular embodiment, there is provided a process for preparing a heparin derivative having signals at 5.95 ppm and 6.15 ppm in the corresponding $^1$H NMR spectrum that each have an intensity (% ratio) of ≤about 4% (e.g. ≤about 3%) relative to the signal at 5.42 ppm of the $^1$H NMR spectrum of unfractionated heparin.

In a particular embodiment, the process defined in the first aspect of the invention comprises minimising the period of time between the completion of step (i) and the start of step (iv).

The skilled person will understand that the maximum period of time between the completion of step (i) and the start of step (iv) acceptable in order to minimise the level of unwanted structural modifications in the heparin derivative will depend on factors such as the temperature of the solution during this period and the concentration of reagents (such as heparin and resulting derivatives thereof) in solution.

In a more particular embodiment, the period of time between the completion of step (i) and the start of step (iv) is a maximum of 6 hours (e.g. a period of from about 2 to about 6 hours).

Pharmaceutical Compositions

As discussed herein, the heparin derivative prepared using the process defined in the first aspect of the invention may be useful in medicine. In particular, pharmaceutical compositions containing such derivatives may be prepared using the heparin derivative obtained from the process of the first aspect of the invention, which compositions may be useful in administration to a patient in order to decrease protracted labour.

Thus, in a second aspect of the invention, there is provided a process for the preparation of a pharmaceutical composition (i.e. a pharmaceutical composition comprising a heparin derivative prepared as defined respect of the first aspect of the invention), comprising the steps of:

(a) preparing a heparin derivative using a process as defined in the first aspect of the invention; and
(b) combining the heparin derivative obtained in step (a) with one or more pharmaceutically acceptable adjuvant, excipient or diluent.

In a particular embodiment, the pharmaceutical composition defined in respect of the second aspect of the invention may be provided in the form of a vial, a pre-filled syringe, an intravenous (IV) solution or a formulation for subcutaneous injection.

The process defined in the first aspect of the invention may have the advantage that it provides a low molecular weight heparin derivative having low anticoagulant activity, which derivative has a low level of unwanted structural modifications resulting from the effect of residual oxidising species retained between process steps. This is achieved by control of the process steps to ensure that reductive conditions are employed within a minimum possible time after completion of the oxidation step.

The process defined in the first aspect of the invention may also have the advantage of being more predictable regarding the molecular weight of the resulting heparin derivative obtained, as a result of residual oxidizing agents having been eliminated. This is because the presence of residual oxidising species (i.e. oxidising species remaining in the heparin derivative as obtained after the completion of the oxidation step, which is referred to herein as step (i)) has been found to lead to non-specific depolymerisation of the heparin derivative, i.e. depolymerisation other than that achieved by alkaline beta elimination (i.e. referred to herein as step (ii)).

The process defined in the first aspect of the invention may also have the advantage that by analysis of the solution in the depolymerisation step (i.e. referred to herein as step (ii)), or by reference to the analysis of a substantially identical depolymerisation process having been previously performed, the skilled person may achieve greater control of the molecular weight of the heparin derivative despite variability in the starting material (e.g. when using different batches of unfractionated heparin).

DESCRIPTION OF THE FIGURES

FIG. 1 shows a graph of the molecular weight of depolymerised heparin obtained over time in Example 2a as provided herein.

EXAMPLES

The present invention may be further illustrated by the following examples.

Example 1

Processes as described herein may be performed using the following general methods.
Oxidation of Glucuronic and Iduronic Acid (Residues), Deletion of Anticoagulant Activity A quantity of about 3000 grams of Heparin (mucosal heparin of Ph. Eur. and USP quality) is dissolved in purified water to obtain a 10-20% w/v solution. The pH of this solution is adjusted to 4.5-5.5. The sodium metaperiodate (NaIO$_4$) is subsequently added to the process solution, with the quantity of periodate being 15-30%, target 25% of the weight of heparin. The pH is again adjusted to 4.5-5.5. The reactor is protected from light. The process solution is reacted for 18-26 hours with constant stirring maintenance of the temperature at 13-17° C. (e.g. about 15° C.), with the temperature being reduced to 5 ° C. during the last two hours.

Depolymerisation of Polysaccharide Chains By An Alkaline Beta Elimination Process While maintaining the temperature at 5-10° C., a NaOH solution is added until a pH of 10.5-11.5 is obtained. The de-polymerization reaction is thereby initiated which leads to a slow decrease of the pH since OH$^-$ ions are neutralised. Thus, the pH is carefully increased and tightly controlled in the range 10.5-11.5 by addition of a NaOH or Na$_2$CO$_3$ solution. Simultaneously, in-process control is initiated to follow the degree of de-polymerization by repeated GPC-HPLC analysis. The reaction proceeds for up to 4 hours or when the optimal molecular weight is obtained. A target range of molecular weight at 5.7-6.3 kDa is preferred. A table (see Example 2) or graph (see FIG. 1) could be used to predict the reaction time needed to obtain the preferred molecular weight range.

The reaction is stopped by slow addition of 4 M HCl until a pH of 5.5-6.5 is obtained.

The molecular weight is determined by GPC-HPLC carried out with a TSK 2000 and TSK 3000 SW columns in series, calibrated using the 1$^{st}$ international standard for LMWH . Refractive index is used to monitor the concentration of the eluate.

Reduction of Iodine Compounds to Iodide and Iodine, Stabilization of the Product By Conversion of Terminal Aldehyde Groups of Polysaccharide to Corresponding Alcohols While maintaining the temperature at 5-17° C., a quantity of 130-200 grams of sodium borohydride is then added in portions, this to avoid over heating by the exothermic reaction, and the pH will increase to 9 (e.g. 10) to 11. The reaction is continued for 14-20 hours. After this reaction time, a dilute acid is added slowly in order to adjust the pH to a value of 4, this degrades remaining sodium borohydride. After maintaining a pH of 4 for 45-60 minutes, the pH of the solution is adjusted to 7 with a dilute NaOH solution.

Precipitation of Reduced Product and Initial Removal of Iodine-Containing Compounds Ethanol (95-99.5%) is added to the reaction mixture over a period of 0.5-1 hour, with careful stirring and at a temperature of 5-25° C. The volume of ethanol to be added is in the range 1-2 volumes of ethanol per volume of process solution. The oxidized heparin is then allowed to precipitate and sediment for 15-20 hours, after which the mother liquor is decanted and discarded. Next, the sediment is dissolved in purified water to obtain a 15-30% w/v process solution. NaCl is added to obtain a concentration of 0.15-0.30 mol/L in the process solution Purification of the Product One volume of process solution is then added to 1.5-2.5 volumes of ethanol (95-99.5%) followed by centrifugation at >2000 G, and at <20° C. for 20-30 minutes, after which the supernatant is decanted and discarded.

The product paste obtained by centrifugation is then dissolved in purified water to obtain a product concentration 10-20% w/v. Then NaCl is added to obtain a concentration of 0.20-0.35 mol/liter. Further on 1.5-2.5 volumes of ethanol (95-99.5%) are added per volume of process solution which precipitates the product from the solution. Centrifugation follows at >2000 G, and at <20° C. for 20-30 minutes after which the supernatant is decanted and discarded.

Next the remaining paste is added purified water to dissolve. The product concentration would now be in the range of 10-20% w/v. The pH of the product solution is now adjusted to 6.5-7.5. The solution is then filtered to remove any particulates. Then, to one volume of process solution is added 1.5-2.5 volumes of ethanol (95-99.5%). Centrifugation follows at >2000 G, and at <20° C. for 20-30 minutes after which the supernatant is decanted and discarded.

Reduction of the Size and Water Content of the Precipitate Paste

A reactor is then filled with ethanol, volume 2 liter. While stirring the ethanol, the precipitate paste is added. The mechanical stirring solidifies the paste and replaces the water present by the ethanol giving a homogenous particle suspension. The stirring is discontinued after 1-2 hours after which the particles are allowed to sediment, then the mother liquor is decanted. This procedure is repeated twice. The precipitate is isolated on a polypropylene (PP) filter cloth. This procedure is repeated two more times. After removal of excessive liquid, the particles are passed through a sieve to obtain smaller and uniform sized particles.

Vacuum Drying and Sieving

The product is distributed evenly onto two pre-weighed trays, and placed in a vacuum cabinet. The pressure is reduced with a vacuum pump, the pressure actually obtained being noted, and the trays are heated to 35-40° C., with constant recording of the temperature. A stream of nitrogen is passed through the drier at this time while maintaining the low pressure in the dryer. After 2-3 days, the trays are removed from the drying cabinet and their weights measured. The drying is then continued for an additional 24 hours, thereafter the trays are taken out and weighed. This procedure is performed to monitor the progress of the drying. When a constant weight is obtained, i.e. no further evaporation is noticed, the drying is considered complete. The dry product is dispensed in 2 layer plastic bags covered by laminated plastic/aluminum foil. Storage is performed in a dry area at a temperature of 20-25° C.

Example 2

The process was performed under three sets of conditions (Examples 2a, 2b and 2c), using two different batches of unfractionated heparin (referred to herein as Batch A and Batch B), under the following general conditions.

Oxidation of Glucuronic and Iduronic Acid (Residues), Deletion of Anticoagulant Activity A quantity of about 25 grams of Heparin was dissolved in purified water to obtain a 15% w/v solution. Then 6.25 gram of sodium metaperiodate (NaIO$_4$) was added to the process solution and the pH was the adjusted to 4.9-5.0. The reactor was protected from light. The process solution was reacted for 22 hours with constant stirring maintenance of the temperature at 15° C., after which the temperature was reduced to 5° C. during the last two hours. The total reaction time was 24 hours.

Depolymerisation of Polysaccharide Chains By an Alkaline Beta Elimination Process While maintaining the temperature at 5-10° C., a NaOH solution was added until a pH of 11-11.5 was obtained. The pH was continuously monitored and adjusted to the pH indicated in respect of Example 2a, 2b and 2c (below) over a period of 250 minutes. The reaction was stopped by slow addition of 4 M HCl until a pH of 5.5-6.5 was obtained. The time needed for adjusting the pH was approximately 15 minutes.

During the reaction time, eleven samples were taken at specified time points during the reaction time. The samples were immediately diluted by a 15 mM phosphate buffer solution and pH adjusted to 7 to stop the ongoing reaction. The samples were then subjected to analysis of the molecular weight by GPC-HPLC, as discussed below. A table was created for each process (see below). The molecular weight was determined by GPC-HPLC carried out with TSK 2000 and TSK 3000 SW columns in series, calibrated using the 1st international standard for LMWH (as discussed herein). A refractive index was used to monitor the concentration of the eluate.

Reduction of Iodine Compounds to Iodide and Iodine, Stabilization of the Product By Conversion of Terminal Aldehyde Groups of Polysaccharide to Corresponding Alcohols While maintaining the temperature at 5-15° C., a quantity of 1.75 gram of sodium borohydride was then added in portions during 30 minutes, this to avoid over heating by the exothermic reaction, and the pH increased to 10. A sample was withdrawn from the solution after completed addition of sodium borohydride and was analysed for molecular weight. The results confirmed that the molecular weight remained unchanged. The reaction continued for 20 hours. After this reaction time, a dilute acid was added until a pH of 4-4.5 was obtained, which degraded remaining sodium borohydride. The formation of hydrogen gas bubbles was noticed, which confirmed that NaBH$_4$ had been initially added in excess of required amount. After maintaining a pH of 4 for 45-60 minutes, the pH of the solution was adjusted to 7 with a dilute NaOH solution.

Precipitation of reduced product and initial removal of iodine-containing compounds Ethanol (95-99.5%) was added to the reaction mixture over a period of 0.5-1 hour, with careful stirring and at a temperature of 5-25 ° C. The volume of ethanol added was 1.5 volumes of ethanol per volume of process solution. The product precipitated out of solution and was separated by centrifugation at approximately 5000 G for 20 minutes. Then the mother liquor was decanted. Next, the product paste was dissolved in purified water to obtain a 15-30% w/v process solution. NaCl was added to obtain a concentration of 0.15-0.30 mol/liter in the process solution. Next, ethanol was added, amount 2 volumes of ethanol per volume of process solution. The product precipitated out of solution and was separated by centrifugation at approximately >2000 G for 20 minutes. Again the mother liquor was decanted.

Next the remaining paste was added purified water to dissolve. The product concentration was now in the range of 15-30% w/v. The pH of the product solution was then adjusted to 6.5-7.5 and then the solution was then filtered to remove any particulates. Then, to one volume of process solution was added 2 volumes of ethanol (95-99.5%). Centrifugation followed at >2000 G, and at <20° C. for 20-30 minutes after which the supernatant was decanted and discarded. The paste was then dehydrated by twice repeated additions and decanting of ethanol and manual grinding of the paste.

Vacuum Drying and Milling

The dehydrated paste was then transferred to a glass flask connected to a vacuum dryer. Drying followed under vacuum at a temperature of 38-40° C. The drying was stopped after approximately 48 hours of drying. Then milling followed after which the final product was dispensed in airtight glass vials.

Analysis of the Depolymerisation Step

The progress of the depolymerisation step was analysed by GPC-HPLC using TSK 2000 and TSK 3000 SW columns in series, calibrated using the 1$^{st}$ international standard for LMWH (using techniques as described herein). The refractive index was used to monitor the concentration of the eluate.

The tables provided in respect of each of Examples 2a to 2c below show the times taken to achieve a particular average molecular weight under the respective reaction conditions. The times indicated in respect of Example 2a are also shown in the graph provided as FIG. 1.

Example 2a

Example 2a was reacted in the depolymerisation reaction at a pH of 11 using Batch A of heparin.

| Sample | Mw (kDa) | Time (min) |
|---|---|---|
| 1 | 12.6 | 0 |
| 2 | 8.5 | 15 |
| 3 | 7.7 | 30 |
| 4 | 7.3 | 45 |
| 5 | 7.0 | 60 |
| 6 | 6.8 | 73 |
| 7 | 6.7 | 84 |
| 8 | 6.2 | 127 |
| 9 | 6.1 | 152 |
| 10 | 5.9 | 210 |
| 11 | 5.8 | 248 |

Example 2b

Example 2b was reacted in the depolymerisation reaction at a pH of 11.5 using Batch A of heparin.

| Sample | Mw (kDa) | Time (min) |
|---|---|---|
| 1 | 13.0 | 0 |
| 2 | 7.3 | 15 |
| 3 | 6.7 | 30 |
| 4 | 6.4 | 45 |
| 5 | 6.2 | 60 |
| 6 | 6.1 | 73 |
| 7 | 6.0 | 84 |
| 8 | 5.7 | 127 |
| 9 | 5.6 | 152 |
| 10 | 5.4 | 210 |
| 11 | 5.3 | 248 |

Example 2c

Example 2c was reacted in the depolymerisation reaction at a pH of 11 using Batch B of heparin.

| Sample | Mw (kDa) | Time (min) |
|---|---|---|
| 1 | 10.4 | 0 |
| 2 | 8.5 | 15 |
| 3 | 7.6 | 30 |
| 4 | 6.6 | 45 |
| 5 | 6.8 | 59 |
| 6 | 6.7 | 69 |
| 7 | 6.5 | 83 |
| 8 | 5.9 | 131 |
| 9 | 6.0 | 152 |
| 10 | 5.7 | 210 |
| 11 | 5.6 | 248 |

Example 3

The below table shows the results of $^1$H NMR analysis of heparin derivatives obtained using the procedure set out in Example 2, following the European Directorate for the Quality of Medicines & Healthcare (EDQM), monograph 7, as set out in the European Pharmacopeia.

| | Intensity (% ratio) compared to the 5.42 ppm signal of unfractionated heparin | |
|---|---|---|
| Sample | 6.15 ppm % of ref. signal | 5.95 ppm % of ref. signal |
| Example 2a | 2.0 | 2.5 |
| Example 2c | 2.5 | 2.0 |

Example 4

The product obtained from processes according to any one of the examples provided herein can be formulated into a pharmaceutical composition by a conventional aseptic process.

In particular, a pharmaceutical composition may be prepared by forming a solution comprising 150 mg/mL of active product and Na phosphate to 15 mM, having a pH of 6-8. The so obtained pharmaceutical composition is intended primarily for subcutaneous administration, but is also suitable for intravenous administration.

The invention claimed is:

1. A process for the preparation of a heparin derivative, the process comprising the consecutive steps of:
   (i) oxidising an acidic aqueous solution of unfractionated heparin by addition of an oxidising agent;
   (ii) depolymerising the oxidised heparin by subjecting the product of step (i) to alkali to form an alkaline solution;
   (iii) maintaining said solution from step (ii) at an alkaline pH for a period of time required to provide depolymerised heparin; and
   (iv) reducing terminal aldehyde groups of said depolymerised heparin by addition of a hydride reducing agent to the solution obtained from step (iii),
   wherein the heparin derivative obtained from said process has a predominantly occurring disaccharide as shown in formula I below

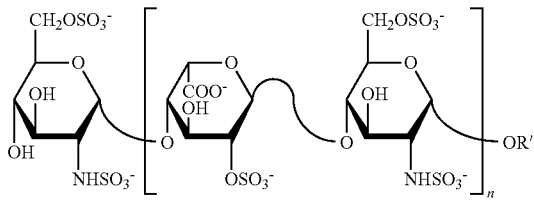

wherein

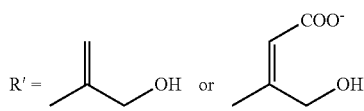

n is an integer from 2 to 20, corresponding to molecular weights between 1.2 and 12 kDa, and the heparin derivative displays signals in the 5.0 ppm to 6.5 ppm region in a $^1$H NMR spectrum with an intensity (% ratio) of less than or equal to about 4% relative to the signal at 5.42 ppm of the $^1$H NMR spectrum of unfractionated heparin, and has a weight average molecular weight of from about 4.6 to about 6.9 kDa and an anti-factor Xa activity of less than about 10 IU/mg;

wherein the period of time between the completion of step (i) and the start of step (iv) is controlled in order to minimise the effect of residual oxidising agents; and wherein said period of time in step (iii) is determined by analysis of said solution, or by reference to a previously-performed substantially identical step (iii).

2. The process as claimed in claim 1, in which, in the heparin derivative, at least 70% of the molecules have a molecular weight of greater than about 3 kDa.

3. The process as claimed in claim 1, in which the heparin derivative comprises polysaccharides with a distribution of cumulative molecular weights as indicated in the table below:

| Molecular mass, kDa | Cumulative weight, % |
| --- | --- |
| >10 | 4-15 |
| >8 | 10-25 |
| >6 | 22-45 |
| >3 | >70. |

4. The process as claimed in claim 1, wherein, in the heparin derivative, the signals in the $^1$H NMR spectrum are present at about 5.95 ppm and about 6.15 ppm.

5. The process as claimed in claim 1, wherein the heparin derivative further has an anti-factor IIa activity of less than 10 IU/mg.

6. The process as claimed in claim 1, wherein, in the heparin derivative, the polysaccharide chains present in the heparin derivative are essentially free of chemically intact saccharide sequences mediating the anticoagulant effect.

7. The process as claimed in claim 1, wherein, after the oxidation step, at least about 90% of non-sulphated vicinal diol moieties in the starting unfractionated heparin have been converted to the corresponding aldehydes.

8. The process as claimed in claim 7, wherein the non-sulphated vicinal diol moieties comprise the iduronic and glucuronic acid residues of heparin.

9. The process as claimed in claim 1, wherein the oxidising agent used in step (i) is sodium metaperiodate.

10. The process as claimed in claim 1, wherein step (i) requires oxidising an aqueous solution of unfractionated heparin by addition of sodium metaperiodate, at a pH of from about 4.5 to about 5.5 and at a temperature below about 25° C.

11. The process as claimed in claim 1, wherein step (ii) requires depolymerising the oxidised heparin by subjecting the product of step (i) to alkali to form a solution having a pH of from about 8 to about 13.

12. The process as claimed in claim 1, wherein the process further comprises the step of:
(iiia) subjecting the solution obtained from step (iii) to acid to form a solution having a pH of from about 5.5 to about 6.5.

13. The process as claimed in claim 1, wherein the reducing agent used in step (iv) is sodium borohydride.

14. The process as claimed in claim 1, wherein the process further comprises the step(s) of:
(iva) quenching the reduction reaction by lowering the pH to form an acidic solution; and, optionally,
(ivb) adjusting the pH of the solution from step (iva) to about neutral.

15. The process as claimed in claim 1, wherein the process further comprises the step of:
(v) recovering the heparin derivative from the solution obtained from step (iv).

16. The process as claimed in claim 1, wherein the period of time between the completion of step (i) and the start of step (iv) is a maximum of 6 hours.

17. The process for the preparation of a pharmaceutical composition comprising a heparin derivative having an average molecular weight of from about 4.6 to about 6.9 kDa and an anti-factor Xa activity of less than about 10 IU/mg, which process comprises the steps of:
preparing a heparin derivative using a process as claimed in claim 1; and
(b) combining the heparin derivative obtained in step (a) with one or more pharmaceutically-acceptable adjuvant, excipient or diluent.

* * * * *

UNITED STATES PATENT AND TRADEMARK OFFICE
CERTIFICATE OF CORRECTION

PATENT NO. : 10,023,659 B2
APPLICATION NO. : 14/898862
DATED : July 17, 2018
INVENTOR(S) : Eriksson et al.

Page 1 of 1

It is certified that error appears in the above-identified patent and that said Letters Patent is hereby corrected as shown below:

In the Claims

Claim 16, at Column 22, Line 38, insert a space between "6" and "hours".

Claim 17, at Column 22, Line 44, insert --(a)-- before "preparing".

Signed and Sealed this
Second Day of October, 2018

Andrei Iancu
*Director of the United States Patent and Trademark Office*